(12) United States Patent
Bergiers et al.

(10) Patent No.: US 9,067,866 B2
(45) Date of Patent: Jun. 30, 2015

(54) RADIATION CURABLE AMINO(METH) ACRYLATES

(75) Inventors: Francis Bergiers, La Hulpe (BE); Thierry Randoux, Braine l'Alleud (BE)

(73) Assignee: ALLNEX BELGIUM S.A., Brussels (BE)

( * ) Notice: Subject to any disclaimer, the term of this patent is extended or adjusted under 35 U.S.C. 154(b) by 386 days.

(21) Appl. No.: 12/226,315

(22) PCT Filed: Jun. 22, 2007

(86) PCT No.: PCT/EP2007/056238
§ 371 (c)(1),
(2), (4) Date: Oct. 15, 2008

(87) PCT Pub. No.: WO2008/000696
PCT Pub. Date: Jan. 3, 2008

(65) Prior Publication Data
US 2009/0318611 A1    Dec. 24, 2009

(30) Foreign Application Priority Data

Jun. 29, 2006    (EP) .................................... 06013453

(51) Int. Cl.
*C07C 229/30*    (2006.01)
*C08L 39/00*    (2006.01)
*G03F 7/027*    (2006.01)
*G03F 7/038*    (2006.01)

(52) U.S. Cl.
CPC .............. *C07C 229/30* (2013.01); *G03F 7/027* (2013.01); *G03F 7/0388* (2013.01)

(58) Field of Classification Search
CPC ...... C07C 229/30; G03F 7/0388; G03F 7/027
USPC .......................................... 524/555; 560/155
See application file for complete search history.

(56) References Cited

U.S. PATENT DOCUMENTS

| | | | |
|---|---|---|---|
| 6,172,129 B1 | 1/2001 | Fan et al. | |
| 6,300,388 B1 | 10/2001 | Verdonck et al. | |
| 6,372,074 B1 * | 4/2002 | Holguin et al. ............... | 156/234 |
| 6,500,878 B1 * | 12/2002 | Reich et al. ................... | 522/100 |
| 6,706,821 B1 | 3/2004 | Letchford | |
| 7,407,707 B2 * | 8/2008 | Gould et al. .................. | 428/418 |
| 2003/0169989 A1 * | 9/2003 | Abel et al. .................... | 385/128 |
| 2005/0245636 A1 * | 11/2005 | Fechter et al. ................ | 522/178 |

FOREIGN PATENT DOCUMENTS

JP    09-143431    6/1997

* cited by examiner

*Primary Examiner* — David W Wu
*Assistant Examiner* — Marie Reddick
(74) *Attorney, Agent, or Firm* — Wenderoth, Lind & Ponack, L.L.P.

(57) ABSTRACT

The invention relates to amino(meth)acrylates obtained from the reaction of amines with a mixture of epoxy(meth)acrylates and (meth)acrylated diluent and there use for making flexible varnishes, coatings, adhesives and inks.

11 Claims, No Drawings

RADIATION CURABLE AMINO(METH) ACRYLATES

This application is the national stage of PCT/EP2007/056238 filed Jun. 22, 2007, and claims foreign priority to EP 06013453.3, filed Jun. 29, 2006.

The present invention relates to amino(meth)acrylates obtained from the addition reaction of (meth)acrylates and amines and their use for making radiation curable compositions useful for making coatings, varnishes, adhesives or inks.

Radiation curable, low viscosity inks and coatings are typically composed of one or more (meth)acrylated monomers and/or oligomers. Epoxy(meth)acrylates have been used in radiation curable compositions since long time because of their good chemical and thermal resistance, adhesion hardness and high reactivity. However, epoxy(meth)acrylates generally also have the drawback of having high viscosity and low flexibility and impact resistance.

In order to improve flexibility and impact resistance, epoxy acrylates can be modified through chain extension for example with butadiene copolymers.

We have now found an alternative way to prepare (meth)acrylates presenting the advantages of epoxy(meth)acrylates as well as improved flexibility.

The present invention therefore relates to amino(meth)acrylates obtained from the reaction of an amine (A) with a mixture comprising from 25 to 99% by weight of at least one epoxy(meth)acrylate (B) comprising at least two (meth)acrylate groups and from 1 to 75% by weight of at least one (meth)acrylated diluent (C).

In the present invention, the term "(meth)acryl" is to be understood as to encompass both acryl and methacryl compounds or derivatives as well as mixtures thereof.

The amine (A) used to prepare the amino(meth)acrylates of the present invention is generally selected from primary amines (A1) comprising at least one primary amino group $-NH_2$ and secondary amines (A2) comprising at least two secondary amino groups $-NH$.

The primary amines (A1) preferably have a molecular weight of 31 to 300, more preferably from 45 to 250. Suitable amines (A1) correspond to formula $R^1-NH_2$ (I) wherein $R^1$ represents an alkyl, optionally substituted by hydroxy, alkoxy, tertiary amine and/or aryl.

Preferred are alkylamines (A1) where the alkyl group comprises from 1 to 30 carbon atoms, preferably from 2 to 18 carbon atoms, optionally substituted by one or more hydroxy groups.

The term "alkyl", as used herein, is defined as including saturated, monovalent hydrocarbon radicals having straight, branched or cyclic moieties or combinations thereof.

Especially preferred are methylamine, ethylamine, propylamine, butylamine, hexylamine, 2-ethylhexylamine, cyclohexylamine, octylamine, dodecylamine, ethanolamine and mixtures thereof.

Suitable secondary amines (A2) correspond to formula $R^2HN-R^4-NHR^3$ wherein $R^2$ and $R^3$ represent, each independently, an alkyl, optionally substituted by hydroxy, alkoxy, tertiary amine and/or aryl, with the proviso that $R^2$ and $R^3$ can be linked in order to form a ring, and $R^4$ is chosen from the group of alkylene and aralkylene chains, containing up to 20 carbon atoms and which may contain from 1 to 8 ether bridges and/or from 1 to 3 tertiary amine bridges. Preferably, $R^4$ is chosen from the group of ethylene, 1,2-propylene, trimethylene, hexamethylene, 2,2-dimethylpropylene, 1-methyltrimethylene, 1,2,3-trimethyltetramethylene, 2-methyl-pentamethylene, 2,2,4-(or 2,4,4-)trimethylhexamethylene, metaxylylene, 3,5,5-trimethylcyclohexyl-1-ene-3-methylene, bis(cyclohexyl-4-ene)methane, bis(4-methylcyclohexyl-3-ene)methane, cyclohexyl-1,3-ene, cyclohexyl-1,4-ene, 1,4-bis(propoxy)-3-ene)butane, N,N-bis(trimethylene)methylamine, 3,6-dioxaoctylene, 3,8-dioxadodecylene, 4,7,10-trioxamidecylene, poly(oxytetramethylene), poly(oxypropylene) with 2 to 15 1,2-propylene oxide units, poly(oxypropylene-co-oxyethylene) with 2 to 15 propylene oxide and 2 to 15 ethylene oxide units, 2,2-dimethylpropylene.

Preferred cyclic secondary amines are diaza-cyclo pentanes, pentenes, hexanes, hexenes, heptanes and heptenes. Especially preferred secondary amines (A2) are piperazine and imidazolidine.

By (meth)acrylated diluent (C) is meant to designate in the present invention, a (meth)acrylated compound wherein the epoxy(meth)acrylate is soluble or miscible therewith.

Preferred (meth)acrylated diluents (C) are those which are liquid at room temperature or which present a viscosity of 1 to 2000 mPa·s at 25° C., especially those having a viscosity of 1 to 200 mPa·s.

Examples of (meth)acrylated diluents (C) are beta-carboxyethyl acrylate, butyl(meth)acrylate, methyl(meth)acrylate, isobutyl (meth)acrylate, 2-ethylhexyl(meth)acrylate, cyclohexyl (meth)acrylate, n-hexyl (meth)acrylate, isobornyl (meth)acrylate, isooctyl (meth)acrylate, n-lauryl (meth)acrylate, octyl/decyl (meth)acrylate, 2-hydroxyethyl(meth)acrylate, phenoxyethyl(meth)acrylate, nonylphenolethoxylate mono(meth)acrylate, 2-(-2-ethoxyethoxy)ethyl(meth)acrylate, 2-butoxyethyl (meth)acrylate, neodecanoic acid glycidyl ester (meth)acrylate, N-vinyl pyrrolidone, 1,6-hexanediol diacrylate (HDDA), pentaerythritoltriacrylate (PETIA), trimethylolpropanetriacrylate (TMPTA), dipropyleneglycol diacrylate (DPGDA), phenylglycidyletheracrylate, and the (meth)acrylated ethoxylated or/and propoxylated derivatives thereof (such as (meth)acrylated ethoxylated or/and propoxylated trimethylolpropane, glycerol, neopentylglycol and/or pentaerythritol).

Preferred (meth)acrylated diluents (C) are those containing at least 2 (meth)acryl groups per molecule. Particularly preferred are di-(meth)acrylates. Generally (meth)acrylates of polyols, especially diols, are used. Acrylates are preferred. Particularly preferred are 1,6-hexanediol diacrylate and dipropyleneglycol diacrylate.

By epoxy(meth)acrylates (B) is meant to designate the (meth)acrylic esters of polyepoxides, i.e. compounds comprising at least two epoxide functions. The epoxy(meth)acrylates (B) used in the present invention are generally those obtained from the esterification reaction of (meth)acrylic acid with polyepoxides. The polyepoxides are generally chosen from glycidyl ethers of aromatic or aliphatic polyols and from cycloaliphatic polyepoxides. Preferred polyepoxides are diglycidylethers of aromatic and aliphatic diols and cycloaliphatic diepoxides, such as diglycidyl ether of bisphenol-A, diglycidyl ether of bisphenol-F, diglycidylether of poly(ethylene oxide-co-propylene oxide), diglycidylether of polypropylene oxide, diglycidylether of hexanediol, diglycidylether of butanediol. Particularly preferred is diglycidyl ether of bisphenol-A.

The mixture used in the present invention preferably comprises from 25 to 75% by weight of epoxy(meth)acrylate (B) and from 25 to 75% by weight of (meth)acrylated diluent (C).

The reaction between (meth)acrylates and amines is known as Michael addition reaction. The reaction between the (meth)acrylates and the amine can take place without any catalyst or solvent. The reaction can be carried out at temperature between −30 to 150° C., the preferred temperature is from 25 to 100° C. Although solvent is not required it may be used to facilitate the heat and mass transfer. The reaction of the acrylates with the amine is preferably carried out in an inert gas atmosphere, for example, under nitrogen or argon, to prevent or minimize unwanted side reactions. However, this is not necessary for a successful reaction.

The amino(meth)acrylates according to the present invention are generally obtained from the reaction of an amine (A) with the mixture comprising epoxy(meth)acrylate (B) and (meth)acrylated diluent (C) in an amount of amine such that the equivalent ratio of amino groups —N—H from the amine (A) to (meth)acrylic double bounds provided by the epoxy (meth)acrylate (B) and the (meth)acrylated diluent (C) is from 0.1 to 0.9. Hence, in case that a primary amine (A1) is used, the number of —N—H groups is calculated as being twice the number of —$NH_2$ groups provided by the primary amine. Preferably the amount of amine (A) is such that the equivalent ratio of amino groups —N—H of (A) to (meth) acrylic double bonds provided by (B) and (C) is at least 0.2, more preferably at least 0.3. The equivalent ratio does preferably not exceed 0.8, more preferably it does not exceed 0.7.

The present invention also relates to a method for the preparation of amino(meth)acrylates such as herein described wherein at least one amine (A) is reacted with a mixture comprising from 25 to 99% by weight of at least one epoxy (meth)acrylate (B) comprising at least two (meth)acrylate groups and from 1 to 75% by weight of at least one (meth) acrylated diluent (C).

Generally a mixture of different amino(meth)acrylates, optionally in the presence of residual (unreacted) (meth)acrylated compounds (B) and/or (C) are obtained.

The completion of the reaction can be followed for example by measuring the amount of free amine. At the completion of the reaction, the amine acrylate can be recovered as residue product; however, in some instances recovery by conventional distillation and fractionation procedures is possible. Preferably the residue of free amine is eliminated from the amino(meth)acrylate at levels below 1000 ppm, more preferably at levels below 500 ppm, especially of at most 200 ppm. Elimination of the free amine can be done by any method suitable therefor, such as stripping, for example with air or nitrogen under reduced pressure. Although it is possible to separate the unreacted (meth)acrylated compounds (B) and/or (C) from the amino(meth)acrylate, generally the (meth)acrylated compounds (B) and/or are not separated from the amino(meth)acrylate before further use in radiation curable compositions.

To prevent premature (meth)acrylate polymerization various inhibitors or stabilizers may also be added during or after the reaction. Typical inhibitors such as aromatic or aliphatic phosphites can be used.

The amino(meth)acrylates of the present invention preferably have a viscosity of 100 to 50000 mPa·s at 25° C., more preferably of 2000 to 20000 mPa·s.

The amino(meth)acrylates of the present invention preferably have a nitrogen content of at least 0.1%, more preferably of at least 1.0%, by weight. The nitrogen content does preferably not exceed 5.0% by weight, more preferably not 3.5%.

The amino(meth)acrylates of the present invention preferably have a content of double bonds (calculated as meq C=C/ g) of 0.1 to 10 meq/g, more preferably of 1 to 5 meq/g.

The present invention also relates to the use of such amino (meth)acrylates, especially in the radiation curable compositions such as described here below.

The amino(meth)acrylates according to the present invention have been found to be very effective in UV/EB curing and can be used alone or along with other (meth)acrylated compounds. The amino(meth)acrylates are readily cured by ultraviolet light radiation or electron beam radiation.

The amino(meth)acrylates according to the invention present a high reactivity.

The amino(meth)acrylates according to the invention permit to obtain coatings presenting a number of beneficial properties such as chemical and thermal resistance, adhesion and hardness. Moreover they also present good flexibility and impact resistance.

The amino(meth)acrylates according to the invention are especially useful for the preparation of inks, more specifically for screen and flexo inks and for the preparation of overprint varnishes.

The amino(meth)acrylates according to the invention are also useful for applications in the electronics market.

The amino(meth)acrylates according to the present invention can be used in radiation curable compositions comprising usual ingredients as sole radiation curable compound or along with other radiation curable, especially (meth)acrylated compounds.

The invention therefore relates to a radiation curable composition containing at least 5% by weight of one or more amino(meth)acrylates according to the invention. Preferably the composition comprises at least 10% by weight of amino (meth)acrylate. The amount of amino(meth)acrylate usually does not exceed 99% by weight.

The radiation curable composition usually contains besides the amino(meth)acrylates, at least one radiation curable polymer precursor other than the amino(meth)acrylates. The term polymer precursor is used to designate a monomer or oligomer or mixtures thereof which have suitable polymerisable functionality, preferably comprising at the chains ends or laterally along the chain, one or more acrylic, methacrylic or vinyl groups. This radiation curable polymer precursor is generally a monomer or oligomer comprising one or more acrylic, methacrylic or vinyl group.

Preferred oligomers include (meth)acrylated acrylic oligomers, aromatic acid (meth)acrylates, (meth)acrylated polybutadienes, (meth)acrylated polyesters, urethane (meth)acrylates, epoxy (meth)acrylates and hyperbranched (meth) acrylates such as hyperbranched polyester polyol (meth) acrylates.

Preferred oligomers are those having a molecular weight of at least 1000 and not more than 6000 Dalton.

When used, the quantity of oligomer in the radiation curable composition is generally at least 5% by weight, preferably at least 10% by weight. The quantity of oligomer does usually not exceed 50% by weight, preferably it does not exceed 40% by weight.

The radiation curable composition can also contain lower molecular weight monomers such as (meth)acrylic acid, beta-carboxyethyl acrylate, butyl(meth)acrylate, methyl(meth) acrylate, isobutyl (meth)acrylate, 2-ethylhexyl(meth)acrylate, cyclohexyl (meth)acrylate, n-hexyl (meth)acrylate, isobornyl (meth)acrylate, isooctyl (meth)acrylate, n-lauryl (meth)acrylate, octyl/decyl (meth)acrylate, 2-hydroxyethyl (meth)acrylate, phenoxyethyl(meth)acrylate, nonylphenolethoxylate mono(meth)acrylate, 2-(-2-ethoxyethoxy)ethyl (meth)acrylate, 2-butoxyethyl (meth)acrylate, cardura (meth)acrylate, N-vinyl pyrrolidone, 1,6-hexanediol diacrylate (HDDA), pentaerythritoltriacrylate (PETIA), trimethylolpropanetriacrylate (TMPTA), phenylglycidyletheracrylate, dipropyleneglycoldiacrylate (DPGDA), tripropyleneglycoldiacrylate (TPGDA) and the (meth)acrylated ethoxylated or/and propoxylated derivatives thereof (such as (meth)acrylated ethoxylated or/and propoxylated trimethylolpropane, glycerol, neopentylglycol and/or pentaerythritol).

The radiation curable compositions used in the present invention generally comprise at least one photoinitiator, that is a compound that can generate radicals by absorption of light, typically UV light. Generally, the amount of photoinitiator in the composition is comprised between 0 and 15% by weight, preferably between 0.01 and 8% by weight.

Alternatively, the radiation curable composition without photoinitiator can be cured, generally by electron beam.

The radiation curable composition can also contain additives commonly used in varnishes, coatings, adhesives and inks, such as substrate wetting agents, anti-foam agents, dispersing agents, flow modification agents, slip agents, plasticizing diluents, fire retardant agents, UV-protection agents, adhesion promoters, reinforcing agents and stabilizers. The total amount of commonly used additives usually does not exceed 10% by weight. Preferably, the composition comprises from 0.01 to 5% by weight of commonly used additives as described here above.

The radiation curable composition can also contain one or more pigment or colorant. The colorants and pigments usable in the compositions of the invention are every pigment known in the art. A list of such pigments can be found in the Color Index. More particularly, those pigments may be cited such as Process Yellow 13 (Diarylide Yellow—Irgalite BAW of Ciba, Permanent GR of Clariant), Process Magenta Pigment 57 (Bona Calcium—Ilobona 4BY of Sun, Irgalite SMA of Ciba), Process Blue 15.3 (Copper Phthalocyanine—Irgalite GLO of Ciba, Hostaperm Blue B2G of Clariant), Process Black 7 (Oxidised Carbon Black—Special Black 250; Special Black 350 of Degussa), etc. The colorants and/or pigments are preferably used at 0-50% by weight of the total weight of the radiation curable composition, more preferably at 0-40% by weight.

The radiation curable composition may also comprise from 0 to 20% by weight of fillers or non reactive diluents or solvents.

The radiation curable compositions can be produced by mixing the selected components thereof by conventional known methods. The blend can be heated, if desired, to facilitate mixing.

The radiation curable compositions as described here above are used for making varnishes, coatings, adhesives and inks. By inks is meant liquid inks as well as paste inks. The radiation curable composition can also be used in stereolithography.

The present invention is illustrated by the following, non-limiting examples.

EXAMPLE 1

To a 1.5 liter double jacketed reactor vessel connected to an oil bath and equipped with a stirrer, was added 470 g of diacrylate ester of bisphenol A epoxy resin (commercialized as EBECRYL®600), 470 g of hexanedioldiacrylate (HDDA), as well as 3.25 g of stabilizer. The reaction mixture was heated and the temperature was set at 40° C. and 60 g of monoethanolamine was added in small portions so that the temperature did not exceed 60° C. After the end of the alimentation, the mixture was heated at 60° C. for two hours until the free amino concentration was lower than 0.2%.

EXAMPLES 2 to 4

Example 1 was repeated except that the amounts and nature of acrylated diluent and amine was changed as specified in Table 1 here below.

The viscosity, content of N and the residual acrylic double bonds of the final aminoacrylates were measured and specified in Table 1.

COMPARATIVE EXAMPLE 5R

Example 3 was repeated except that DGPDA was omitted during the reaction. A solid product was obtained. This product was further diluted with 50 wt % of DPGDA.

COMPARATIVE EXAMPLE 6R

Example 3 was repeated except that the epoxyacrylate was omitted. To 42 wt % of the reaction product of DPGDA (85.3 wt %) and MEA (14.3 wt %) was added 58 wt % of diacrylate ester of bisphenol A epoxy resin.

COMPARATIVE EXAMPLE 7R

Example 1 was repeated except that the epoxyacrylate was omitted. To 39 wt % of the reaction product of HDDA (84.75 wt %) and MEA (15.25 wt %) was added 61 wt % of diacrylate ester of bisphenol A epoxy resin.

COMPARATIVE EXAMPLE 8R

Example 1 was repeated except that the epoxyacrylate was omitted. To 50 wt % of the reaction product of HDDA (83.5 wt %) and MEA (16.5 wt %) was added 50 wt % of diacrylate ester of bisphenol A epoxy resin.

TABLE 1

|  | Ex 1 | Ex 2 | Ex 3 | Ex 4 | CEx. 5R | CEx. 6R | CEx. 7R | CEx. 8R |
| --- | --- | --- | --- | --- | --- | --- | --- | --- |
| Epoxyacrylate (g) | 470 | 409 | 470 | 409 |  |  |  |  |
| Acrylated diluent |  HDDA | HDDA | DPGDA | DPGDA |  |  |  |  |
| (g) | 470 | 409 | 470 | 409 |  |  |  |  |
| Amine | MEA | DDA | MEA | DDA |  |  |  |  |
| (g) | 60 | 182 | 60 | 182 |  |  |  |  |
| % N | 1.38 | 1.35 | 1.38 | 1.35 | 0.69 | 1.37 | 1.37 | 2 |
| Acrylic double bonds meq/g | 4 | 3.25 | 3.8 | 3 | 5.8 | 3.15 | 3.71 | 3.9 |

TABLE 1-continued

|  | Ex 1 | Ex 2 | Ex 3 | Ex 4 | CEx. 5R | CEx. 6R | CEx. 7R | CEx. 8R |
|---|---|---|---|---|---|---|---|---|
| Viscosity (Pas) | 6.2 | 2.6 | 18.6 | 6.0 | 3 | 105 | 30 | 26 |

DPGDA: dipropyleneglycoldiacrylate
MEA: Monoethanolamine
DDA: Dodecylamine
Viscosity is measured by cone and plate at 25° C.

Films of 50 μm thickness were made using the aminoacrylates of Examples 1 to 4 and Comparative Examples 5R to 8R and cured under EB light of 5 mrad-250 eV at 50 mm/min. Stress-strain curves have been recorded and are represented in Table 2. A composition comprising 70% by weight of the aminoacrylate of Example 2 and 30% by weight of HDDA was also evaluated according to the same test and reported in Table 2.

TABLE 2

|  | Young modulus (Mpa) | Force at 5% elongation | Force at brake (Mpa) | Strain at brake (%) |
|---|---|---|---|---|
| Example 1 | 817 | 24 | 28 | 15 |
| Example 2 | 134 | 4 | 11 | 23 |
| Example 3 | 800 | 14 | 20 | 35 |
| Example 4 | 71 | 2 | 8 | 34 |
| Comp. Ex. 5R | 2084 | 53 | 50 | 4.5 |
| Comp. Ex. 6R | 1376 | 37 | 38 | 10 |
| Comp. Ex. 7R | 1300 | 33 | 32 | 11 |
| Comp. Ex. 8R | 277 | 7 | 16 | 26 |
| 70 wt % AA Ex. 2 + 30 wt % HDDA | 5482 | 16 | 20 | 11 |

The results in Table 2 show that the mixtures obtained in Comparative Examples are less flexible than the aminoacrylates according to the invention.

The invention claimed is:

1. An amino(meth)acrylate produced by a method which comprises:
    reacting a primary or secondary amine (A) with a mixture comprising from 25 to 99% by weight of at least one epoxy(meth)acrylate (B) comprising at least two (meth)acrylate groups and from 1 to 75% by weight of at least one (meth)acrylated diluent (C), based on a total weight of the mixture of (B) and (C), wherein (B) is different from (C),
    wherein the amine (A) is selected from primary amines (A1) comprising at least one primary amino group —$NH_2$ and secondary amines (A2) comprising at least two secondary amino groups —NH, and
    wherein the amino(meth)acrylates have a nitrogen content of at least 1.0% by weight.

2. The amino(meth)acrylate according to claim 1 wherein the amine (A1) is represented by formula $R^1$—$NH_2$ wherein $R^1$ is an alkyl, optionally substituted by hydroxy, alkoxy, tertiary amine and/or aryl.

3. The amino(meth)acrylate according to claim 1, wherein the epoxy(meth)acrylate (B) is selected from a reaction product of (meth)acrylic acid and at least one polyepoxide selected from a diglycidylether of an aromatic or aliphatic polyol and from a cycloaliphatic polyepoxide.

4. The amino(meth)acrylate according to claim 3 wherein the epoxy(meth)acrylate (B) is a reaction product of (meth)acrylic acid and diglycidyl ether of bisphenol A.

5. The amino(meth)acrylate according to claim 1 wherein the (meth)acrylated diluent (C) is selected from those which are liquid at room temperature or which exhibit a viscosity of 1 to 2000 mPa·s at 25° C.

6. The amino(meth)acrylate according to claim 1 wherein an amount of amine (A) used is such that an equivalent ratio of —N—H groups provided by amine (A) to (meth)acrylic double bonds provided by epoxy(meth)acrylate (B) and methacrylated diluent (C) is from 0.1 to 0.9.

7. The amino(meth)acrylate according to claim 1 having a content of double bonds of 0.1 to 10 meq/g.

8. A radiation curable composition containing from 5% to 99% by weight of at least one amino(meth)acrylate according to claim 1, based on a total weight of the radiation curable composition.

9. A method for preparation of a radiation curable composition suitable for preparation of coatings, inks or varnishes comprising the steps of:
    (i) providing an amino (meth) acrylate produced by a method which comprises reacting a primary or secondary amine (A) with a mixture comprising from 25 to 99% by weight of at least one epoxy(meth)acrylate (B) comprising at least two (meth)acrylate groups and from 1 to 75% by weight of at least one (meth)acrylated diluent (C), based on a total weight of the mixture of (B) and (C), wherein (B) is different from (C),
    wherein the amine (A) is selected from primary amines (A1) comprising at least one primary amino group —$NH_2$ and secondary amines (A2) comprising at least two secondary amino groups —NH,
    wherein the amino(meth)acrylates have a nitrogen content of at least 1.0% by weight, and
    (ii) incorporating said amino (meth) acrylate into a radiation curable composition that is suitable for use as a coating, ink or varnish.

10. The method according to claim 9 wherein said radiation curable composition contains at least one additive suitable for use in coatings, inks or varnishes.

11. The method according to claim 10 wherein said at least one additive is present in an amount of up to 10% by weight of said radiation curable composition.

* * * * *